US006913599B2

(12) United States Patent
Mishima et al.

(10) Patent No.: US 6,913,599 B2
(45) Date of Patent: Jul. 5, 2005

(54) DISPOSABLE UNDERGARMENT

(75) Inventors: Yoshitaka Mishima, Kagawa-ken (JP);
Miyuki Ikeda, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 115 days.

(21) Appl. No.: 10/016,411

(22) Filed: Dec. 10, 2001

(65) Prior Publication Data

US 2002/0072726 A1 Jun. 13, 2002

(30) Foreign Application Priority Data

Dec. 12, 2000 (JP) .......................................... 2000-377441

(51) Int. Cl.[7] .................................................. A61F 13/15
(52) U.S. Cl. ............................. 604/385.08; 604/385.19; 604/385.28
(58) Field of Search ....................... 604/385.22, 385.19, 604/385.08, 385.28

(56) References Cited

U.S. PATENT DOCUMENTS

| | | | | |
|---|---|---|---|---|
| 3,532,093 | A | | 10/1970 | Lovret |
| 5,269,775 | A | | 12/1993 | Freeland et al. |
| 5,304,159 | A | * | 4/1994 | Tanji et al. ............. 604/385.19 |
| 5,342,342 | A | * | 8/1994 | Kitaoka ................. 604/385.19 |
| 5,429,632 | A | * | 7/1995 | Tanji et al. ............. 604/385.28 |
| 5,669,896 | A | * | 9/1997 | Kielpikowski ......... 604/385.28 |
| 5,672,166 | A | * | 9/1997 | Vandemoortele ....... 604/385.28 |
| 5,947,947 | A | | 9/1999 | Tanzer et al. |
| 6,458,114 | B1 | * | 10/2002 | Mishima et al. ....... 604/385.24 |
| 6,497,693 | B1 | * | 12/2002 | Otsubo .................. 604/385.19 |
| 6,527,756 | B1 | * | 3/2003 | Mishima et al. ....... 604/385.19 |
| 2001/0023342 | A1 | * | 9/2001 | Suekane ................ 604/385.24 |

FOREIGN PATENT DOCUMENTS

| | | |
|---|---|---|
| EP | 0 904 758 | 3/1999 |
| EP | 0 908 162 | 4/1999 |
| EP | 1 034 760 | 9/2000 |
| EP | 1 174 102 | 1/2002 |
| GB | 2 280 374 | 2/1995 |
| JP | 2-121662 | 5/1990 |
| JP | 09-238979 | 9/1997 |

OTHER PUBLICATIONS

Copy of European Search Report dated May 6, 2002.

* cited by examiner

*Primary Examiner*—Larry I. Schwartz
*Assistant Examiner*—C. Lynne Anderson
(74) *Attorney, Agent, or Firm*—Butzel Long

(57) ABSTRACT

A disposable undergarment that includes an absorbent panel and a stretchable skin-facing sheet positioned on a skin-facing side of the panel. The skin-facing sheet has fixed regions lying on longitudinally opposite end regions of the undergarment, a middle region normally biased to be spaced apart upward from the panel, transversely opposite side edge regions transversely inward to define leg-holes and an opening formed in the middle region in a manner that a basis weight of the skin-facing sheet is higher in the transversely opposite side edge regions than in the remaining region and a tensile stress of the skin-facing sheet is higher in the transversely opposite side edge regions than in the remaining region.

7 Claims, 9 Drawing Sheets

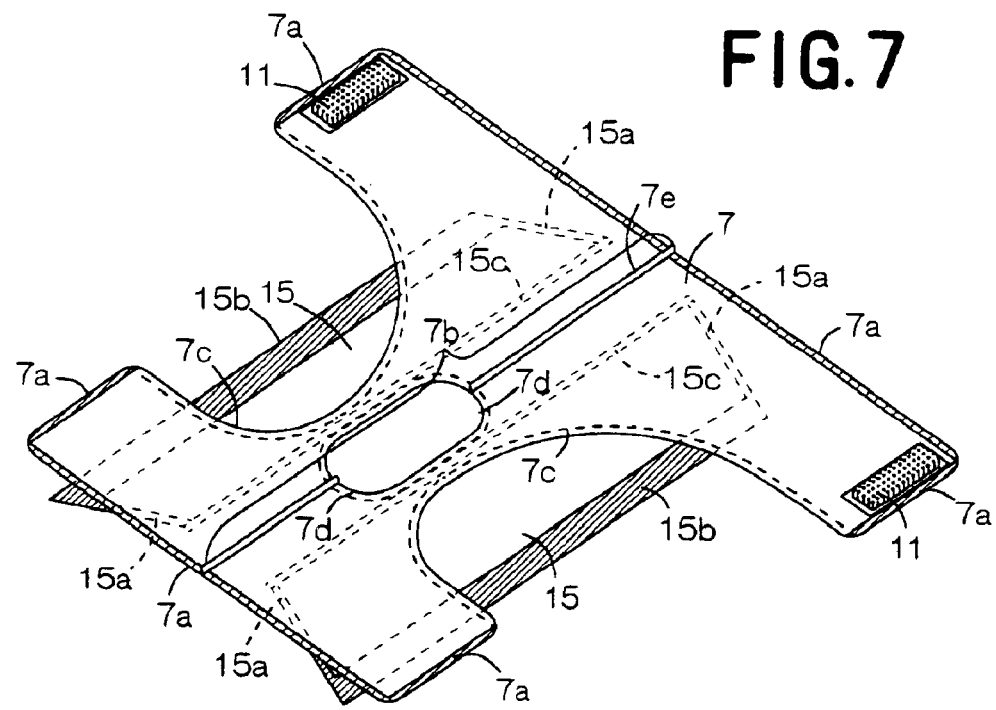
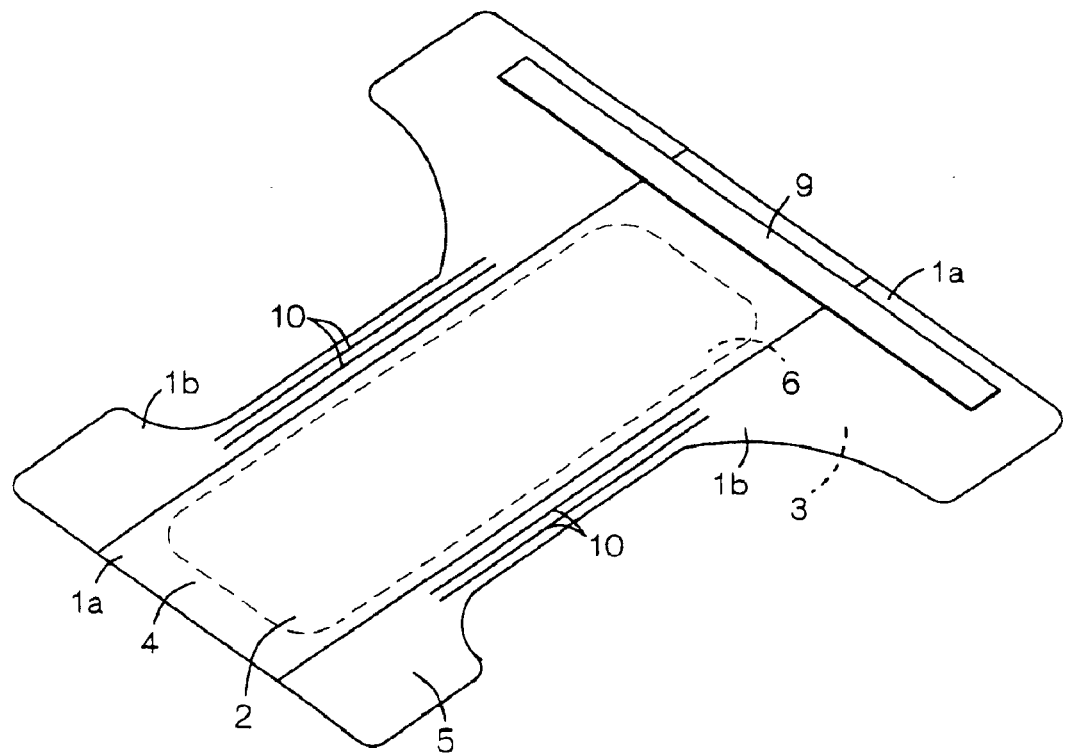
FIG. 7

DISPOSABLE UNDERGARMENT

This invention relates to a disposable undergarment for absorption and containment of body wastes.

Japanese Patent Application Publication No. 1990-121662A discloses a disposable diaper comprising a liquid-impervious base sheet, an elastically stretchable liquid-impervious skin-facing sheet, and a liquid-absorbent panel disposed between the base sheet and the skin-facing sheet and joined to the base sheet. The skin-facing sheet has its peripheral edge portion joined to a peripheral edge portion of the base sheet. The skin-facing sheet has an opening formed in the vicinity of its longitudinal center line. With this diaper of prior art, a space is formed between the skin-facing sheet and the panel as the diaper is worn so that body wastes may be received through the opening of the skin-facing sheet into the space. According to the disclosure in this publication, the skin-facing sheet disposed between the wearer's skin and the panel prevents the body wastes once received in the space apart from sticking to the wearer's skin.

In the case of the diaper disclosed in the publication, the skin-facing sheet has its peripheral edge portion joined to a peripheral edge portion of the base sheet, so the skin-facing sheet moves in conformity with a movement of the base sheet caused by a movement of the diaper wearer. Consequently, it is impossible to keep the skin-facing sheet stably in the wearer's crotch region. If the skin-facing sheet slides off the wearer's crotch region, the opening of this skin-facing sheet also slides off its desired position corresponding to the wearer's excretive organs and the excretion discharged onto the opening-free region of the skin-facing sheet may sticking to the wearer's skin.

It is an object of this invention to provide a disposable undergarment in which the skin-facing sheet can be stably kept in close contact with its wearer's skin in the wearer's crotch region and reliably prevent any amount of body wastes held on the skin-facing surface from sticking to the wearer's skin.

According to this invention, there is provided a disposable undergarment having longitudinally opposite end regions and transversely opposite side regions, comprising a liquid-impervious base sheet defining a non-skin-facing side and a liquid-absorbent panel placed upon the base sheet and defining a skin-facing side opposed to the non-skin-facing side.

The undergarment further comprises an elastically stretchable and substantially liquid-impervious skin-facing sheet is attached to the skin-facing side so as to cover the panel, the skin-facing sheet having fixed regions lying on the longitudinally opposite end regions and joined to the skin-facing side, a longitudinally middle region extending between the fixed regions and normally biased to be spaced apart upward from the panel as the undergarment is curved in a longitudinal direction thereof with the skin-facing sheet inside, a pair of transversely opposite side regions curving transversely inward on both sides of the longitudinally middle region so as to define a pair of leg-holes and at least one opening formed in the longitudinally middle region; and a basis weight of the skin-facing sheet being higher in the transversely opposite side regions for the leg-holes than in a remaining region of the skin-facing sheet and a tensile stress of the skin-facing sheet is higher in the transversely opposite side regions for the leg-holes than in the remaining region.

This invention may be embodied in other manners as described below:

A basis weight of the skin-facing sheet is higher in a peripheral edge region of the opening than a remaining region of the skin-facing sheet and a tensile stress of the skin-facing sheet is higher in the peripheral edge region of the opening than in the remaining region.

A bulging line extends on the skin-facing sheet in the longitudinal direction in vicinity of a longitudinal center line of the skin-facing sheet and wherein the bulging line is formed by folding overlappingly a part of the surface of the skin-facing sheet facing opposed to the skin-facing side and joining the part together.

The skin-facing sheet is folded back at least once along the transversely opposite side regions to define the leg-holes and the peripheral edge region of the opening so as to increase the basis weight and the tensile stress of the skin-facing sheet in the transversely opposite side regions and the peripheral edge region of the opening.

There are further provided a pair of substantially liquid-impervious leak-barrier sheets extending in the longitudinal direction along the transversely opposite side regions of the undergarment and disposed between the base sheet and the skin-facing sheet, each of these leak-barrier sheets having longitudinally opposite fixed end regions joined to the longitudinally opposite end regions of the undergarment, a fixed bottom region joined to each of the transversely opposite side regions of the undergarment and a fixed top region joined to the surface of the skin-facing sheet opposite to this leak-barrier sheet.

The leak-barrier sheets are elastically stretchable and the skin-facing sheet as well as the leak-barrier sheets are attached under extension in the longitudinal direction to the skin-facing side of the undergarment.

The transversely opposite side edge regions of the skin-facing sheet to define the leg-holes lie inside the transversely opposite side regions of the base sheet.

FIG. 7 is an exploded perspective view of the diaper in FIG. 6;

Details of a disposable undergarment according to this invention will be more fully understood with descriptions of an open-type diaper given hereunder in reference to the accompanying drawings as one embodiment of this invention.

Figure 1:
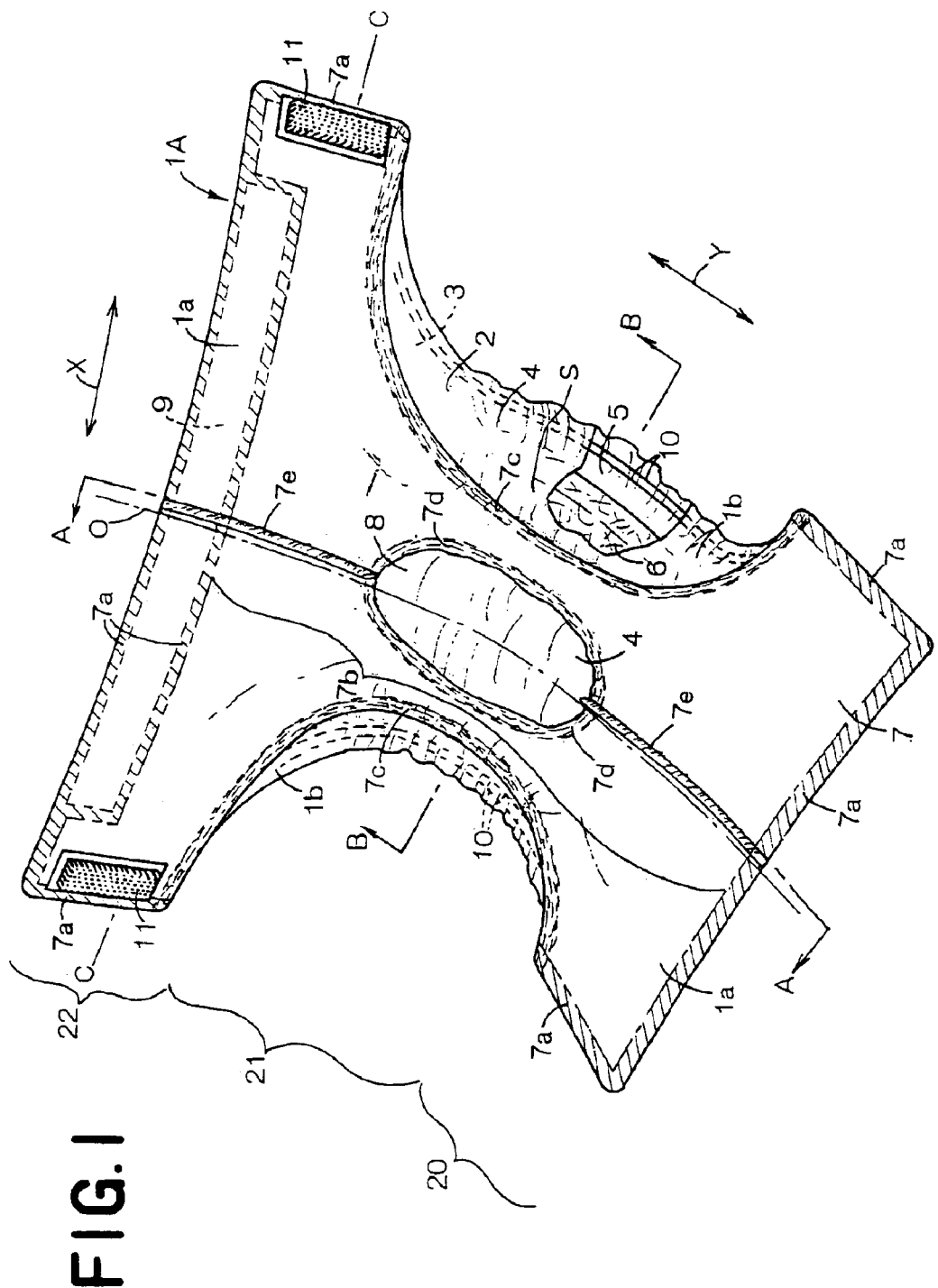
FIG. 1 is a partially cutaway perspective view of a diaper viewed from skin-contacting surface side thereof.
Figure 2:
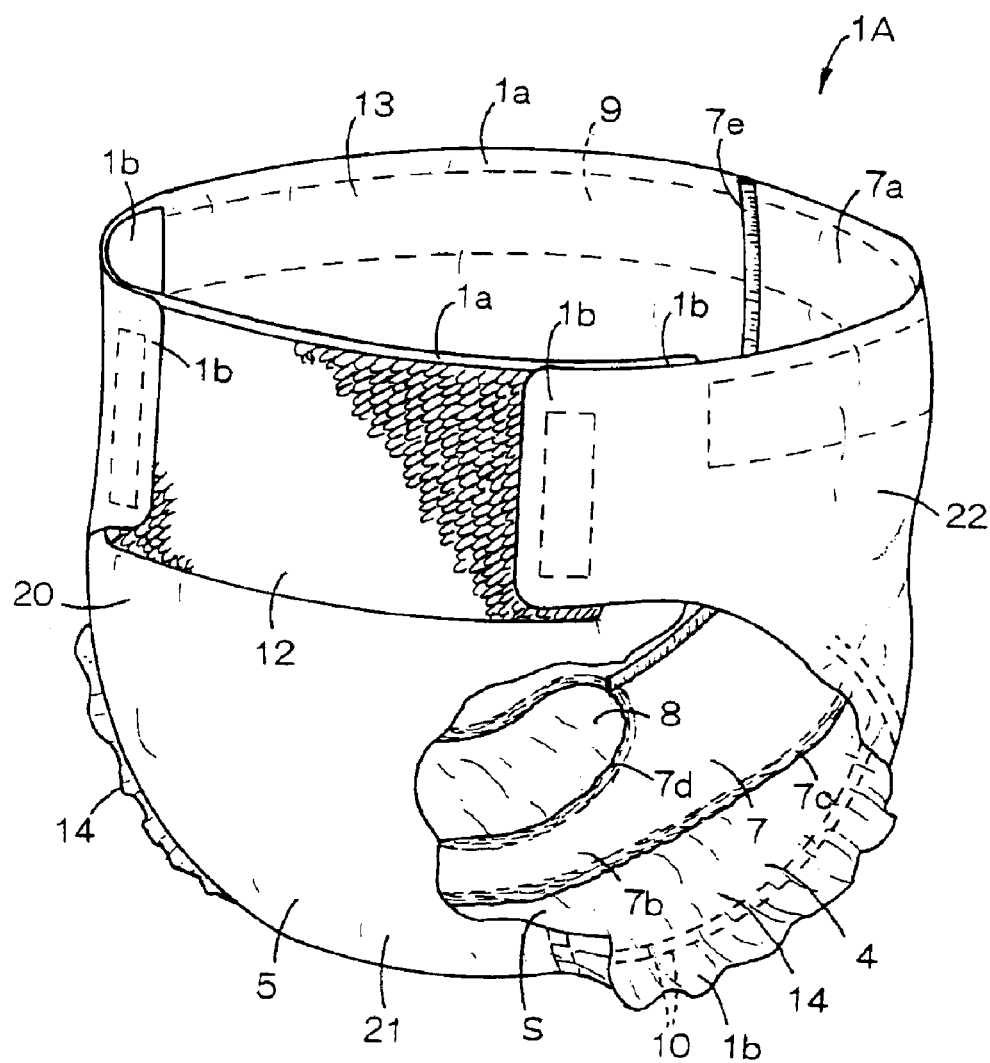
FIG. 2 is a partially cutaway perspective view of the diaper as being worn with front and rear waist regions thereof connected to each other.
Figure 3:
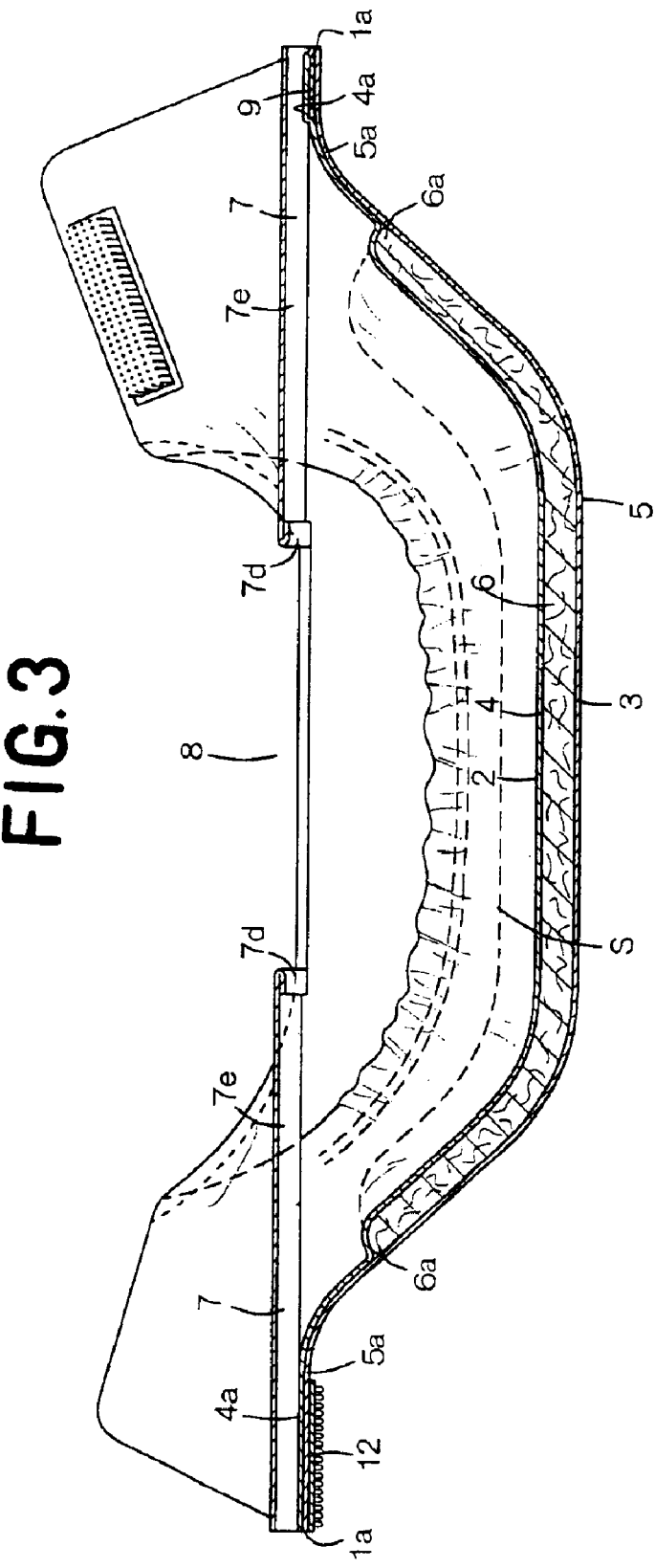
FIG. 3 is a cross-sectional view taken along a line A—A in FIG. 1.
Figure 4:
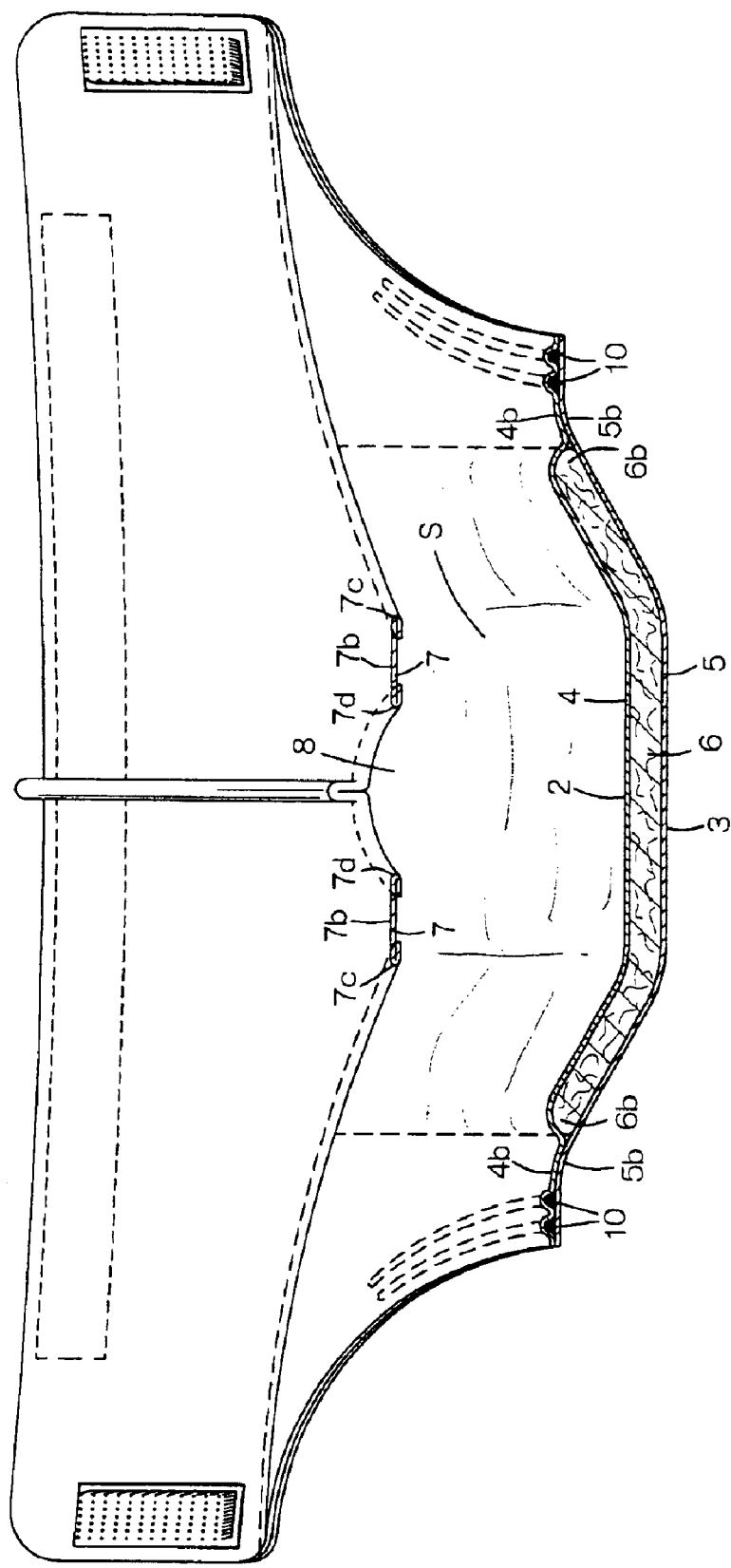
FIG. 4 is a cross-sectional view taken along a line B—B in FIG. 1.
Figure 5:
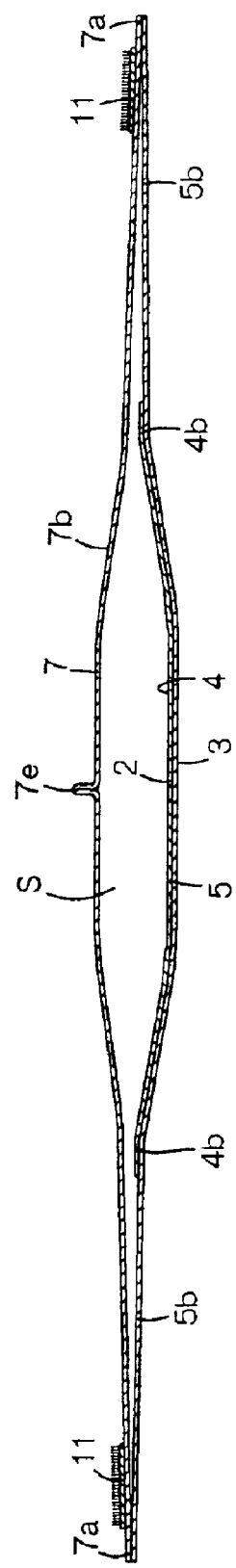
FIG. 5 is a sectional view taken along a line C—C in FIG. 1.

FIG. 1 is a partially cutaway perspective view showing a diaper 1A from skin-facing surface 2 thereof, FIG. 2 is a partially cutaway perspective view showing the diaper 1A as being worn with front and rear waist regions 20, 22 thereof connected to each other, FIG. 3 is a sectional view taken along a line A—A in FIG. 1, FIG. 4 is a sectional view taken along a line B—B in FIG. 1 and FIG. 5 is a sectional view taken along a line C—C in FIG. 1. In FIG. 1, a longitudinal direction is indicated by an arrow Y and a transverse direction is indicated by an arrow X. The side of the diaper 1A referred to herein as the skin-facing side 2 should be understood to be the side of the diaper 1A intended to be in contact with the wearer's skin and the side of the diaper 1A referred to herein as a non-skin-facing side 3 should be understood to be the side of the diaper 1A intended to be out of contact with the wearer's skin when the diaper 1A is worn.

The diaper 1A comprises a liquid-pervious topsheet 4, a liquid-impervious base sheet 5 and a liquid-absorbent panel 6 disposed between these topsheet 4 and base sheet 5. This panel 6 is entirely covered with and joined to tissue paper (not shown). The panel 6 is joined to the topsheet 4 as well as to the base sheet 5 with the tissue paper lying therebetween. In addition to these sheets 4, 5 and panel 6, the diaper 1A comprises substantially liquid-impervious skin-facing sheets 7.

The diaper 1A is composed, in the longitudinal direction, of a front waist region 20, a rear waist region 22 and a crotch region 21 extending between these front and rear waist regions 20, 22. The diaper 1A is contoured by longitudinally opposite end regions 1a extending in the transverse direction and transversely opposite side regions 1b extending in the longitudinal direction. In the crotch region 21, the transversely opposite side edge regions 1b curve transversely inward in a shape of a substantially circular arc. Of the diaper 1A, the topsheet 4 defines the skin-facing side 2 and the base sheet 5 defines the non-skin-contacting side 3.

In the rear waist region 22, a ribbon-like elastic member 9 extending in the transverse direction is attached under extension to the end portion 1a so that this elastic member 9 may be operatively associated with a waist-hole. Along the transversely opposite side edge regions 1b, a plurality of elastic members 10 extending in the longitudinal direction are attached under extension to the diaper 1A so that these elastic members 10 may be operatively associated with respective leg-holes.

The skin-facing sheet 7 is formed of a fibrous nonwoven fabric being elastically stretchable in the transverse direction as well as in the longitudinal direction and attached under extension in the longitudinal direction to the skin-facing side 2 of the diaper 1A. The skin-facing sheet 7 has fixed regions 7a defined along the longitudinally opposite end regions 1a and a longitudinally middle free region 7b extending between the fixed regions 7a. The longitudinally middle region 7b covers the panel 6 indirectly, i.e., with the topsheet 4 lying therebetween. The fixed regions 7a of the skin-facing sheet 7 are joined to the topsheet 4.

Along transversely opposite side edges of the middle free region 7b of the skin-facing sheet 7, a pair of transversely opposite side edge regions 7c curve transversely inward in a shape of a substantially circular arc. The middle region 7b of the skin-facing sheet 7 is formed with an opening 8 which is dimensioned to be larger in the longitudinal direction so that the topsheet 4 may be partially exposed in this opening 8.

The opposite side edge regions 7c of the skin-facing sheet 7 lie inside the opposite side edge regions 1b of the diaper 1A and the minimum dimension of the skin-facing sheet 7 in the middle region 7b is smaller than the minimum dimension of the diaper 1A in the transverse direction, i.e., between the opposite side edge regions 1b of the diaper 1A. The middle region 7b of the skin-facing sheet 7 is spaced apart upward from the panel 6 under the extensional force of the skin-facing sheet 7 as the diaper 1A is curved in the longitudinal direction with the topsheet 4 inside.

The skin-facing sheet 7 is formed with a bulging line 7e extending in the longitudinal direction in the vicinity of a longitudinal center line O of the skin-facing sheet 7. The bulging line 7e is formed by folding overlappingly a part of the surface of the skin-facing sheet 7 with its surface facing the topsheet 4 and then bonding this part together.

Along the opposite side edge regions 7c and a peripheral edge portion 7d of the opening 8, the skin-facing sheet 7 is folded toward its surface facing the topsheet 4 back onto itself and intermittently joined to itself. Such a unique arrangement results in that a basis weight of the skin-facing sheet 7 is higher in the opposite side edge regions 7c and the peripheral edge portion 7d of the opening 8 than in its remaining portion and a tensile stress of the skin-facing sheet 7 also is higher in these opposite side edge regions 7c and peripheral edge portion 7d than in the remaining portion.

On the transversely opposite side regions of the rear waist region 22, the skin-facing sheet 7 is provided with a pair of hook members 11. In the front waist region 20, the base sheet 5 is provided with a rectangular loop member 12 which is dimensioned to be larger in the transverse direction. This loop member 12 defines an engaging zone for the hook members 11.

To wear the diaper 1A, the transversely opposite side edge regions 1b in the rear waist region 22 may be placed upon the outer side of the transversely opposite side edge regions 1b in the front waist region 20, then the respective hook members 11 may be engaged with the loop member 12 to connect the front waist region 20 with the rear waist region 22.

A waist-hole 13 and a pair of leg-holes 14 are defined in the diaper 1A, as seen in FIG. 2, as the front and rear waist regions 20, 22 are connected to each other in the manner as described above. The diaper 1A curves in the longitudinal direction with the topsheet 4 inside and the middle region 7b of the skin-facing sheet 7 is spaced apart upward from the panel 6.

In the diaper 1A, a space S is formed between the topsheet 4 and the skin-facing sheet 7. The longitudinally opposite side end regions 1a extend in a circumferential direction around the wearer's waist and the transversely opposite side edge regions 1b as well as the transversely opposite side edge regions 7c extend in the circumferential direction around the wearer's thighs as the diaper 1A is worn.

The middle region 7b of the skin-facing sheet 7 spaced apart upward from the panel 6 as the diaper 1A is worn is stabilized in close contact with the wearer's crotch region, so it is not apprehended that the skin-facing sheet 7 might slide away from the wearer's crotch region even if the diaper 1A is moved due to movement of the diaper 1A. In this way, the skin-facing sheet 7 maintained in close contact with the wearer's skin in the wearer's crotch region serves to prevent the body wastes from sticking to the wearer's skin.

The transversely opposite side edge regions 7c of the skin-facing sheet 7 lie inside the transversely opposite side edge regions 1b of the diaper 1A and therefore the minimum dimension of the middle region 7b in the transverse direction is smaller than the minimum dimension between the transversely opposite side edge regions 1b. This arrangement also is advantageous to maintain the skin-facing sheet 7 in close contact with the wearer's skin in the wearer's crotch region and thereby to prevent the wearer from having an uncomfortable feeling.

As has already been described, the tensile stress of the skin-facing sheet 7 is sufficiently higher in its transversely opposite side edge regions 7c than in its remaining portion, therefore, these side edge regions 7c press tightly with the high tensile stress against the wearer's thighs and thereby to improve a stability of fit of the skin-facing sheet 7 to the wearer's skin in the wearer's crotch region.

In the skin-facing sheet 7, if the peripheral edge portion 7d of the opening 8 is distorted to form pleats or gathers therealong and the topsheet 4 contacts with the skin-facing sheet 7, any amount of body wastes such as urine or loose excretion held on the topsheet 4 would flow along these pleats or gathers and stick to the wearer's skin. However, the diaper 1A according to this invention well overcomes this problem by its unique arrangement such that the basis weight of the skin-facing sheet 7 is higher in the peripheral edge potion 7d of the opening 8 than the remaining portion and the tensile stress of the skin-facing sheet 7 also is higher in the peripheral edge portion 7d than the remaining region. Specifically, the peripheral edge portion 7d of the opening 8 is resistant to formation of those pleats or gathers and therefore the anxiety that the body wastes might flow beyond the peripheral edge portion 7d of the opening 8 and stick to the wearer's skin can be minimized.

The transversely opposite side edge regions 7c of the skin-facing sheet 7 as well as the peripheral edge portion 7d of the opening 8 are not provided with elastically stretchable members bonded under extension thereto. Therefore, the opposite side edge regions 7c as well as the peripheral edge portion 7d are free from formation of a plurality of gathers which might uncomfortably irritate the wearer's skin.

In the diaper 1A, the bulging line 7e extending on the skin-facing sheet 7 in the longitudinal direction is received in the cleft of the wearer's buttock as the diaper 1A is worn. In this way, the bulging line 7e limits movement of the skin-facing sheet 7 in the transverse direction and thereby prevents the skin-facing sheet 7 from moving sideways.

Along the longitudinally opposite end regions 1a, the longitudinally opposite end regions 4a, 5a of the topsheet 4 and the base sheet 5, respectively, extend longitudinally outward beyond the longitudinally opposite ends of the panel 6 and the end regions 4a, 5a of these sheets 4, 5 are placed upon and joined to each other as seen in FIG. 3. The elastic member 9 operatively associated with the waist-hole is disposed between the topsheet 4 and the base sheet 5 and joined to these sheets 4, 5.

Along the transversely opposite side edge regions 1b of the diaper 1A in the crotch region 21, the transversely opposite side edge regions 4b, 5b of the topsheet 4 and the base sheet 5, respectively, extend transversely outward beyond the transversely opposite side edges 6b of the panel 6 and the side edge regions 4b, 5b of these sheets 4, 5 are placed upon and joined to each other, as seen in FIG. 4. The elastic members 10 operatively associated with the leg-holes are disposed between the topsheet 4 and the base sheet 5 and joined to these sheets 4, 5.

Along the transversely opposite side edge regions 1b of the diaper 1A in the rear waist region 22, the transversely opposite side regions 5b of the base sheet 5 and the skin-facing sheet 7 extend transversely outward beyond the transversely opposite side edge regions 4b of the topsheet 4 as seen in FIG. 5.

Figure 6:
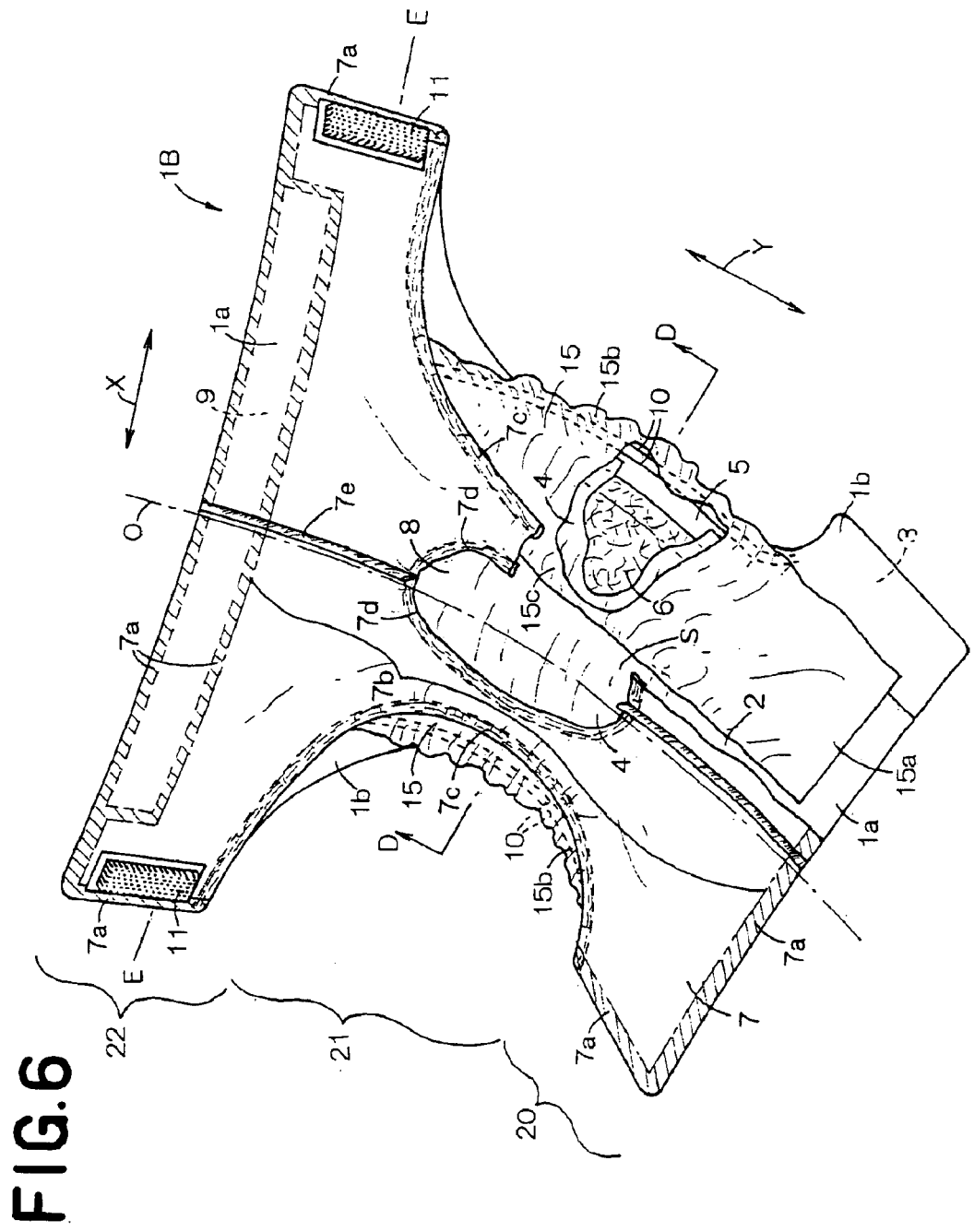
FIG. 6 is a partially cutaway perspective view showing another embodiment of the diaper.
Figure 8:
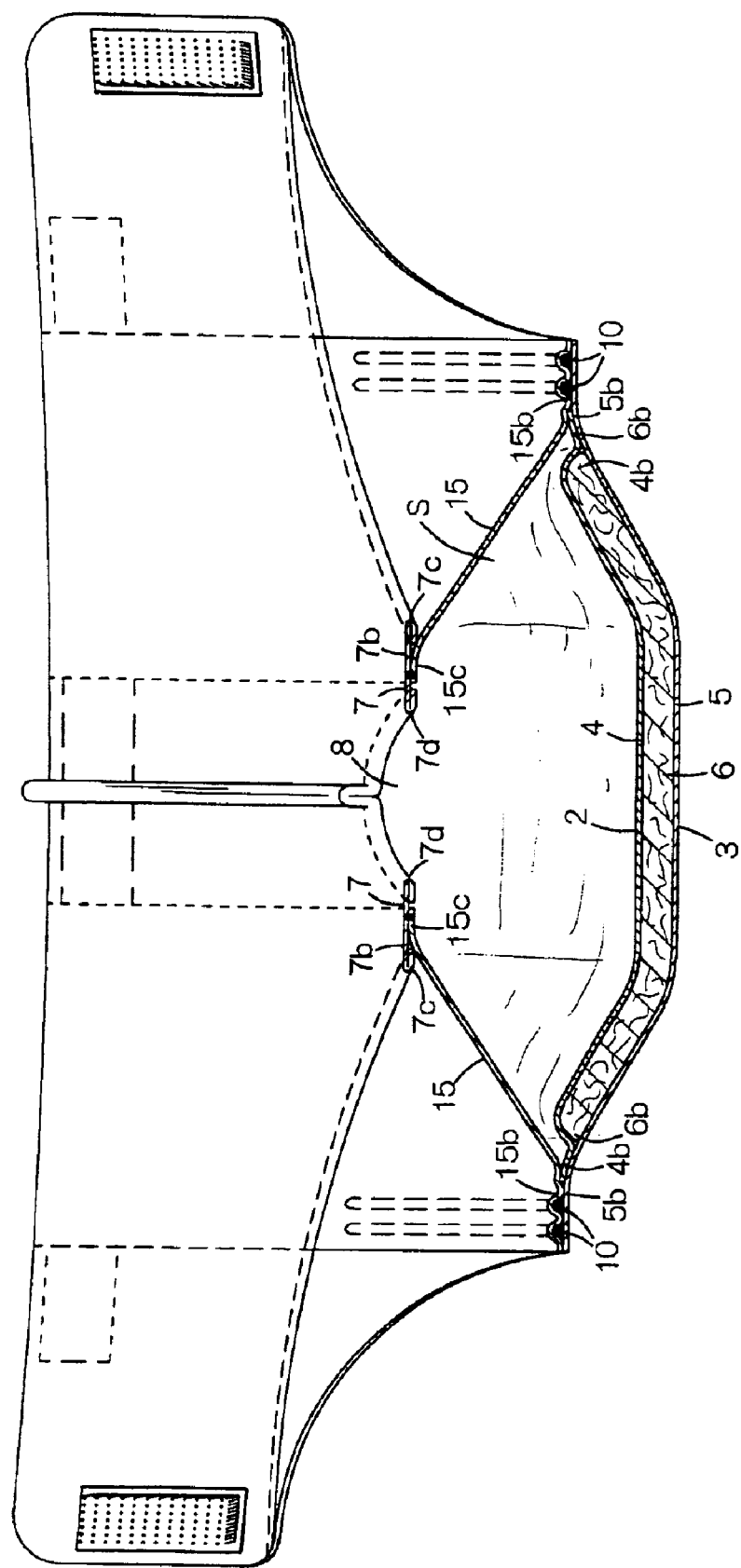
FIG. 8 is a cross-sectional view taken along a line D—D in FIG. 6.

FIG. 6 is a partially cutaway perspective view showing a diaper 1B according to another embodiment of this invention, FIG. 7 is an exploded perspective view showing this diaper 1B, FIG. 8 is a sectional view taken along a line D—D in FIG. 6 and FIG. 8 is a sectional view taken along a line E—E in FIG. 6. In FIG. 6, a longitudinal direction is indicated by an arrow Y and a transverse direction is indicated by an arrow X. The diaper 1B shown by FIG. 6 is distinguished from the diaper 1A shown in FIG. 1 in arrangement as will be described.

This diaper 1B is provided with leak-barrier sheets 15 formed of a fibrous nonwoven fabric being elastically stretchable in the transverse direction as well as in the longitudinal direction. These leak-barrier sheets 15 are disposed between the topsheet 4 and the skin-facing sheet 7 so as to be spaced apart from each other in the transverse direction and to extend in the longitudinal direction. The skin-facing sheet 7 and the leak-barrier sheets 15 are attached under extension in the longitudinal direction to the skin-facing surface side of the diaper 1B.

These leak-barrier sheets 15 respectively have longitudinally opposite fixed end regions 15a joined to the longitudinally opposite end regions 1a of the diaper 1B, respectively, fixed bottom regions 15b joined to the transversely opposite side edge regions 1b of the diaper 1B and fixed top regions 15c joined to the surface of the skin-facing sheet 7 opposed to these leak-barrier sheets 15.

The skin-facing sheet 7 has the fixed regions 7a lying along the longitudinally opposite end regions 1a and the longitudinally middle region 7b extending between the fixed regions 7a. The skin-facing sheet 7 has the pair of transversely opposite side edge regions 7c intended to define the respective leg-holes and extending on both sides of the middle region 7b. The longitudinally middle region 7b is formed with the opening 8 dimensioned to be larger in the longitudinal direction. The fixed regions 7a of the skin-facing sheet 7 are joined to the topsheet 4 and the base sheet 5.

Upon wearing, the diaper 1B curves in the longitudinal direction with the topsheet 4 inside and the middle region 7b of the skin-facing sheet 7 is spaced apart upward from the panel 6 under the effect of the tension of the sheet 7. Simultaneously, the leak-barrier sheets 15 contract in the longitudinal direction and rise between the topsheet 4 and the skin-facing sheet 7. As shown in FIG. 8, the space S is defined within the diaper 1B by the topsheet 4, the skin-facing sheet 7 and the leak-barrier sheets 15.

Along the transversely opposite side edge regions 1b of the diaper 1B in the crotch region 21, the transversely opposite side edge regions 4b of the topsheet 4 extend transversely outward slightly beyond the transversely opposite side edges 6b of the panel 6, and side edge regions 5b of the base sheet 5 and the fixed bottom regions 15b of the respective leak-barrier sheets 15 further extend transversely outward beyond the side edge regions 4b of the topsheet 4, as seen in FIG. 8. The side edge regions 4b are disposed between the side regions 5b and the fixed bottom regions 15b and joined to them. The side edge regions 5b and the fixed bottom regions 15b are placed upon and joined to each other. The elastic members 10 operatively associated with the leg-holes are disposed between the base sheet 5 and the leak-barrier sheets 15 and joined to these sheets 5, 15.

Figure 9:
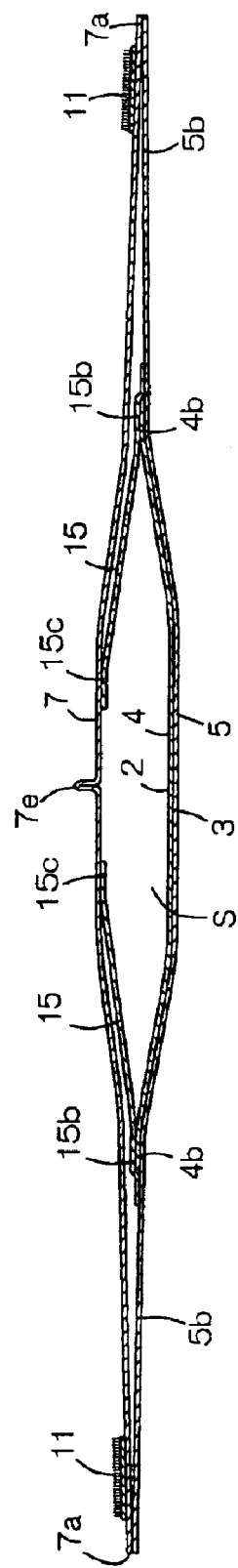
FIG. 9 is a sectional view taken along a line E—E in FIG. 6.

As shown in FIG. 9, along the transversely opposite side edge regions 1b of the diaper 1B in the rear waist region 22, the transversely opposite side regions 5b of the base sheet 5 and the skin-facing sheet 7 extend transversely outward beyond the fixed bottom regions 15b of the respective leak-barrier sheets 15. The leak-barrier sheets 15 tilt transversely inward from the fixed bottom regions 15b toward the fixed top regions 15c, respectively.

With this diaper 1B, the free side edge regions 6b of the leak-barrier sheets 15 rising on the topsheet 4 form barriers against body wastes such as urine or loose excretion which may spread over the topsheet 4 and reach the transversely opposite side edge regions 1b of the diaper 1B and these barriers reliably prevent such body wastes from leaking beyond the respective side edge regions 1b. Furthermore, the diaper 1B enables the skin-facing sheet 7 to prevent the body wastes from sticking to the wearer's skin.

The skin-facing sheet 5 and the leak-barrier sheets 15 may be formed from an elastically stretchable hydrophobic fibrous nonwoven fabric obtained by melt blown or spun bond process. Components of such elastic stretchable nonwoven fabric may be stretchable fibers obtained by melting and spinning thermoplastic elastomer resin. The elastically stretchable fibrous nonwoven fabric may be a composite nonwoven fabric consisting of a hydrophobic fibrous nonwoven fabric made of thermoplastic elastomer resin fibers and a hydrophobic fibrous nonwoven fabric comprising crimped fibers which are obtained by melting and spinning thermoplastic synthetic resin such as polypropylene, polyethylene or polyester bonded to at least one surface of the hydrophobic fibrous nonwoven fabric.

The topsheet 4 may be formed of a hydrophilic fibrous nonwoven fabric or finely porous plastic film. The base sheet 5 may be formed of a hydrophobic fibrous nonwoven fabric, liquid-impervious plastic film, two-layered hydrophobic nonwoven fabric, or composite sheet consisting of a hydrophobic fibrous nonwoven fabric laminated with a plastic film.

It is also possible to form the base sheet 5 by having a composite nonwoven fabric with high water-resistant property made of melt blown process sandwiched by nonwoven fabrecs having high strength and flexibility made of spun bond process.

The nonwoven fabric used as a stock material for the topsheet 4 and the base sheet 5 may be selected from a group of materials obtained by spun lacing, needle punching, melt blowing, thermal bonding, spun bonding, chemical bonding and air-through processes. The component fiber of such nonwoven fabric may be selected from a group of materials of polyolefine-, polyester- and polyamide-fibers, and core-sheath type conjugated fibers or side-by-side type conjugated fibers of polyethylene/polypropylene or polyethylene/polyester.

The panel 6 is composed of a mixture of fluff pulp and super absorptive polymer particles or a mixture of fluff pulp, super absorptive polymer particles and thermoplastic synthetic resin fiber compressed to a desired thickness. The super absorptive polymer may be selected from a group of materials of starch-based polymer, cellulose-based polymer and synthetic polymer.

For the diaper 1B of FIG. 6, the presence of the topsheet 4 is not essential so far as the base sheet 5 has the liquid-absorbent panel 6 attached thereto. In this case, the panel 6 preferably comprises a fibrous web with appropriate compressive restoring elasticity, which contains the super absorptive polymer particles dispersed and retained in fiber-interstices thereof and which has been compressed to a desired thickness to give a desired shape-stability. The component fiber of such fibrous web may be selected from a group of materials of polyolefine-based fibers such as polypropylene or polyethylene, polyester-based fiber such as polyethylene terephthalate, polyamide-based fibers such as nylon 66 or nylon 6, acryl-based fibers, and cellulose-based fibers such as pulp, rayon or acetate.

In the diaper 1B of FIG. 6, it is also possible to form the leak-barrier sheets 15 from an inelastic hydrophobic fibrous nonwoven fabric. In this case, the fixed top regions of the leak-barrier sheets 15 may be joined to the surface of the skin-facing sheet 7 under extension in the longitudinal direction with its surface opposited to the leak-barrier sheets 15 and then the skin-facing sheet 7 may be attached under extension in the longitudinal direction to the skin-facing side 2 of the diaper 1B.

In both the diaper 1A and the diaper 1B, the skin-facing sheet 7 may be formed in the middle region 7b with two openings. In this case, these openings are preferably formed in the front waist region 20 and the rear waist region 22, respectively, so that these openings may be located corresponding to the positions of urinary organs and anus, respectively, as the diaper 1A or 1B is worn.

Bonding between the topsheet 4 and the base sheet 5, fixing of the skin-facing sheets 7 and the leak-barrier sheets 15 to these sheets 4, 5, joining of the panel 6, and attachment of the respective elastic members 9, 10 may be achieved by using hot melt adhesive or heat welding technique such as heat-sealing or sonic-sealing.

This invention is applicable not only to an open-type diaper but also to a pants-type diaper having its front and rear waist regions previously connected to each other.

With the disposable undergarment according to this invention, the longitudinally middle region of the skin-facing sheet is spaced apart upward from the liquid-absorbent panel by extensional force of the skin-facing sheet and comes in close contact with the wearer's skin in the wearer's crotch region as the undergarment curves in the longitudinal direction with its skin-facing surface inside. While the article is worn, there is no anxiety that the skin-facing sheet might slide from the wearer's crotch region even if the undergarment moves due to a movement of the wearer. In the undergarment according to this invention, the substantially liquid-impervious skin-facing sheet adapted to be placed closely against the wearer's crotch region is disposed between the wearer's skin and the skin-facing surface, so there is no anxiety that any amount of urine or loose excretion held on the skin-facing surface might stick to the wearer's skin.

With the undergarment according to this invention, as the skin-facing sheet is reliably coincided with the wearer's crotch region, the article is worn without an uncomfortable feeling as has often been experienced by the wearer. In addition, the transversely opposite side edge regions of the skin-facing sheet tightly press the wearer's thighs so as to improve the stability with which the skin-facing sheet can be placed in close contact with the wearer's crotch region. Furthermore, the undergarment according to this invention is uniquely constructed so that the peripheral edge portion of the opening formed in the skin-facing sheet can be resistant to formation of pleats or gathers, and the body wastes possibly sticking to the peripheral edge portion of the opening can be minimized.

With the embodiment of the undergarment according to which the skin-facing sheet is formed with the bulging line extending in the longitudinal direction, this bulging line serves to restrict movement of the skin-facing sheet in the transverse direction and thereby prevents the skin-facing sheet from unacceptably shifting sideways.

With the embodiment of the undergarment according to which a pair of leak-barrier sheets are provided so as to extend in the longitudinal direction along the transversely opposite side edge regions of the undergarment, these leak-barrier sheets rise between the skin-facing surface and the skin-facing sheet so as to form barriers as the undergarment is worn. These barriers reliably prevent any amount of body wastes from leaking beyond the transversely opposite side edge regions of the article even after the body wastes have spread on the skin-facing surface to these transversely opposite side edge regions.

What is claimed is:

1. A disposable undergarment having longitudinally opposite end regions and transversely opposite side regions and comprising:

a liquid-impervious base sheet defining a non-skin-facing side;

a liquid-absorbent panel placed upon said base sheet;

a liquid-previous topsheet placed upon said liquid-absorbent panel and defining a skin-facing side opposed to said non-skin-facing side; and an elastically stretchable and substantially liquid-impervious skin-facing sheet attached to said skin-facing side of said liquid-pervious topsheet so as to cover said liquid-absorbent panel, said skin-facing sheet having:
fixed regions lying on said longitudinally opposite end regions and joined to said skin-facing side of said liquid-pervious topsheet;
a longitudinally middle region extending between said fixed regions and normally biased lobe spaced apart upward from said liquid-absorbent panel as said undergarment is curved in a longitudinal direction thereof with the skin-facing side of said liquid-pervious topsheet inside;
a pair of transversely opposite side regions curving transversely inward on both sides of said longitudinally middle region so as to define a pair of leg-holes; and
at least one opening formed in said longitudinally middle region, longitudinally opposite end regions of said liquid-pervious topsheet and said skin-facing sheet being substantially coextensive in a transverse direction, a longitudinal central portion of the skin-facing sheet having a width that is smaller than a width of an underlying central portion of the liquid-pervious topsheet so that transverse opposite outer terminal side edges of the liquid-pervious topsheet and of said skin-facing sheet at the longitudinal central portion are not coextensive with one another in the transverse direction and the transverse opposite outer terminal side edges of the skin-facing sheet at the longitudinal central portion are spaced apart upward and inward from the transverse opposite outer terminal side edges of the liquid-pervious topsheet at the longitudinal central portion as said undergarment is curved in a longitudinal direction thereof with the skin-facing side of said liquid-pervious sheet inside, a basis weight of said skin-facing sheet being higher in said transversely opposite side regions defining the leg-holes than a basis weight of a remaining region of said skin-facing sheet and a tensile stress of said skin-facing sheet is higher than a tensile stress of said transversely opposite side regions defining the leg-holes than in the remaining region.

2. The disposable undergarment according to claim 1, wherein a basis weight of said skin-facing sheet is higher in a peripheral edge region of said at least one opening than a basis weight of the remaining region and a tensile stress of said skin-facing sheet is higher in said peripheral edge region of said at least one opening than a tensile stress of the remaining region.

3. The disposable undergarment according to claim 1, wherein a bulging line extends on said skin-facing sheet in said longitudinal direction in a vicinity of a longitudinal center line of said skin-facing sheet and wherein said bulging line is formed by folding and overlapping a part of said skin-facing sheet and joining said part together.

4. The disposable undergarment according to claim 3, wherein said skin-facing sheet is folded back at least once along said transversely opposite side regions defining the leg-holes and said peripheral edge region of said at least one opening so as to increase the basis weight and the tensile stress of said skin-facing sheet in said transversely opposite side regions and in said peripheral edge region of said at least one opening.

5. The disposable undergarment according to claim 1, further including a pair of substantially liquid-impervious leak-barrier sheets extending in the longitudinal direction along said transversely opposite side regions of said undergarment and disposed between said base sheet and said skin-facing sheet, each of said leak-barrier sheets having longitudinally opposite fixed end regions joined to said longitudinally opposite end regions of said undergarment, a fixed bottom region joined to each of said transversely opposite side regions of said undergarment and a fixed top region joined to the surface of said skin-facing sheet opposite to each of the leak-barrier sheets.

6. A disposable undergarment having longitudinally opposite end regions and transversely opposite side regions and comprising:

a liquid-impervious base sheet defining a non-skin-facing side;

a liquid-absorbent panel placed upon said base sheet;

a liquid-previous topsheet placed upon said liquid-absorbent panel and defining a skin-facing side opposed to said non-skin-facing side; and an elastically stretchable and substantially liquid-impervious skin-facing sheet attached to said skin-facing side of said liquid-pervious topsheet so as to cover said liquid-absorbent panel;

said skin-facing sheet having:
fixed regions lying on said longitudinally opposite end regions and joined to said skin-facing side of said liquid-pervious topsheet;
a longitudinally middle region extending between said fixed regions and normally biased to be spaced apart upward from said liquid-absorbent panel as said undergarment is curved in a longitudinal direction thereof with the skin-facing side of said liquid-pervious topsheet inside;
a pair of transversely opposite side regions curving transversely inward on both sides of said longitudinally middle region so as to define a pair of leg-holes; and
at least one opening formed in said longitudinally middle region, longitudinally opposite end regions of said liquid-pervious topsheet and said skin-facing sheet being substantially coextensive in a transverse direction, a longitudinal central portion of the skin-facing sheet having a width that is smaller than a width of an underlying central portion of the liquid-pervious topsheet so that transverse opposite outer terminal side edges of the liquid-pervious topsheet and of said skin-facing sheet at the longitudinal central portion are not coextensive with one another in the transverse direction and the transverse opposite outer terminal side edges of the skin-facing sheet at the longitudinal central portion are spaced apart upward and inward from the transverse opposite outer terminal side edges of the liquid-pervious topsheet at the longitudinal central portion as said undergarment is curved in a longitudinal direction thereof with the skin-facing side of said liquid-pervious sheet inside, a basis weight of said skin-facing sheet being higher in said transversely opposite side regions defining the leg-holes than a basis weight of a remaining region of said skin-facing sheet and a tensile stress of said skin-facing sheet is higher than a tensile stress of said transversely opposite side regions defining the leg-holes than in the remaining region, wherein said leak-barrier sheets are elastically stretchable and wherein said skin-facing sheet and said leak-barrier sheets are attached under tension in said longitudinal direction to said skin-facing side of said liquid-previous top-sheet.

7. The disposable undergarment according to claim 1, wherein said transversely opposite side regions of said skin-facing sheet defining the leg-holes lie inwardly of said transversely opposite side regions of said base sheet.

* * * * *